(12) United States Patent
Usher (10) Patent No.: US 7,744,632 B2
(45) Date of Patent: Jun. 29, 2010

(54) ROD TO ROD CONNECTOR

(75) Inventor: John A. Usher, West Palm Beach, FL (US)

(73) Assignee: Aesculap Implant Systems, Inc., Center Valley, PA (US)

( * ) Notice: Subject to any disclaimer, the term of this patent is extended or adjusted under 35 U.S.C. 154(b) by 132 days.

(21) Appl. No.: 11/937,915

(22) Filed: Nov. 9, 2007

(65) Prior Publication Data

US 2008/0177315 A1    Jul. 24, 2008

Related U.S. Application Data

(60) Provisional application No. 60/870,856, filed on Dec. 20, 2006.

(51) Int. Cl.
  *A61B 17/70* (2006.01)
(52) U.S. Cl. ...................................... 606/250; 606/278
(58) Field of Classification Search .................. 606/60, 606/246–279; 403/396, 398; *A61B 17/70*
See application file for complete search history.

(56) References Cited

U.S. PATENT DOCUMENTS

| 3,865,105 | A | 2/1975 | Lode |
| 4,349,017 | A | 9/1982 | Sayegh |
| 4,361,144 | A | 11/1982 | Slatis |
| 4,483,334 | A | 11/1984 | Murray |
| 4,648,388 | A | 3/1987 | Stefee |
| 4,719,905 | A | 1/1988 | Stefee |
| 4,747,400 | A | 5/1988 | Koeneman |
| 4,768,524 | A | 9/1988 | Hardy |
| 4,794,918 | A | 1/1989 | Wolter |

| 4,944,743 | A | 7/1990 | Gotzen |

(Continued)

FOREIGN PATENT DOCUMENTS

DE    39 24 050 A1    1/1991

(Continued)

OTHER PUBLICATIONS

U.S. Appl. No. 11/937,915, filed Nov. 9, 2007, Usher.

(Continued)

*Primary Examiner*—Eduardo C Robert
*Assistant Examiner*—Lynnsy Schneider
(74) *Attorney, Agent, or Firm*—RatnerPrestia (57) ABSTRACT

An apparatus for coupling a spinal rod to a cross bar comprising a main body having a channel with a wall for receiving a spinal rod therein, an opening for receiving a fastener with at least one tang adjacent to the opening, a clamping body pivotally disposed in the main body, the clamping body being moveable between a first position in which it does not clamp the spinal rod in the channel and a second position in which it does clamp the spinal rod in the channel, a cross bar having an opening aligned substantially with the opening of the main body and having the tang disposed therein, and a fastener for rigidly coupling the cross bar to the main body, the fastener being positioned within the openings of the cross bar and the main body, wherein the fastener is operable to force the tang into the cross bar to clamp the cross bar to the main body and simultaneously to move the clamping body between the first position and the second position.

21 Claims, 4 Drawing Sheets

U.S. PATENT DOCUMENTS

| | | | |
|---|---|---|---|
| 5,002,542 A | 3/1991 | Frigg | |
| 5,005,562 A | 4/1991 | Cotrel | |
| 5,030,220 A | 7/1991 | Howland | |
| 5,053,034 A | 10/1991 | Olerud | |
| 5,074,864 A | 12/1991 | Cozad | |
| 5,084,048 A | 1/1992 | Jacob | |
| 5,084,049 A | 1/1992 | Asher et al. | |
| 5,098,432 A | 3/1992 | Wagenknecht | |
| 5,102,412 A | 4/1992 | Rogozinski | |
| 5,112,232 A | 5/1992 | Cray | |
| 5,116,334 A | 5/1992 | Cozad | |
| 5,147,359 A | 9/1992 | Cozad | |
| 5,154,718 A | 10/1992 | Cozad | |
| 5,176,678 A | 1/1993 | Tsou | |
| 5,181,917 A | 1/1993 | Rogozinski | |
| 5,196,013 A | 3/1993 | Harms | |
| 5,201,374 A | 4/1993 | Rahm | |
| 5,207,678 A | 5/1993 | Harms | |
| 5,254,118 A | 10/1993 | Mirkovic | |
| 5,257,993 A | 11/1993 | Asher | |
| 5,261,907 A | 11/1993 | Vignaud et al. | |
| 5,261,913 A | 11/1993 | Marnay | |
| 5,275,600 A | 1/1994 | Allard | |
| 5,304,179 A | 4/1994 | Wagner | |
| 5,306,275 A | 4/1994 | Bryan | |
| 5,312,405 A | 5/1994 | Korotko et al. | |
| 5,330,473 A | 7/1994 | Howland | |
| 5,334,203 A | 8/1994 | Wagner | |
| 5,352,224 A | 10/1994 | Westermann | |
| 5,374,267 A | 12/1994 | Siegal | |
| 5,380,325 A | 1/1995 | Lahille | |
| 5,382,248 A | 1/1995 | Jacobson | |
| 5,395,370 A | 3/1995 | Muller | |
| 5,397,363 A | 3/1995 | Gelbard | |
| 5,403,316 A | 4/1995 | Ashman | |
| 5,413,602 A | 5/1995 | Metz-Stavenhagen | |
| 5,437,669 A | 8/1995 | Yuan | |
| 5,468,241 A | 11/1995 | Metz-Stavenhagen | |
| 5,470,333 A | 11/1995 | Ray | |
| 5,474,555 A | 12/1995 | Puno | |
| 5,476,464 A | 12/1995 | Metz-Stavenhagen et al. | |
| 5,487,742 A | 1/1996 | Cotrel | |
| 5,498,263 A | 3/1996 | DiNello et al. | |
| 5,507,745 A | 4/1996 | Logroscino | |
| 5,507,746 A | 4/1996 | Lin | |
| 5,514,132 A | 5/1996 | Csernatony | |
| 5,522,816 A | 6/1996 | Dinello et al. | |
| 5,527,314 A | 6/1996 | Brumfield | |
| 5,531,745 A | 7/1996 | Ray | |
| 5,531,747 A | 7/1996 | Ray | |
| 5,534,002 A | 7/1996 | Brumfield | |
| 5,536,268 A | 7/1996 | Griss | |
| 5,545,164 A | 8/1996 | Howland | |
| 5,545,166 A | 8/1996 | Howland | |
| 5,545,167 A | 8/1996 | Lin | |
| 5,549,607 A | 8/1996 | Olson | |
| 5,562,660 A | 10/1996 | Grob | |
| 5,562,662 A | 10/1996 | Brumfield | |
| 5,562,663 A | 10/1996 | Wisnewski | |
| 5,569,246 A | 10/1996 | Ojima | |
| 5,569,247 A | 10/1996 | Morrison | |
| 5,601,552 A | 2/1997 | Cotrel | |
| 5,609,594 A | 3/1997 | Errico | |
| 5,609,992 A | 3/1997 | Sorori | |
| 5,611,800 A | 3/1997 | Davis et al. | |
| 5,613,968 A | 3/1997 | Lin | |
| 5,620,444 A | 4/1997 | Assaker | |
| 5,624,442 A | 4/1997 | Mellinget et al. | |
| 5,630,816 A | 5/1997 | Kambin | |
| 5,643,259 A | 7/1997 | Sasso | |
| 5,651,789 A | 7/1997 | Cotrel | |
| 5,653,708 A | 8/1997 | Howland | |
| 5,667,506 A | 9/1997 | Sutterlin | |
| 5,667,507 A | 9/1997 | Corin | |
| 5,669,910 A | 9/1997 | Korhonen et al. | |
| 5,672,176 A | 9/1997 | Biedermann | |
| 5,676,665 A | 10/1997 | Bryan | |
| 5,676,703 A | 10/1997 | Gelbard | |
| 5,683,393 A | 11/1997 | Ralph | |
| 5,688,272 A * | 11/1997 | Montague et al. | ........... 606/252 |
| 5,688,275 A | 11/1997 | Korios | |
| 5,702,452 A | 12/1997 | Argenson | |
| 5,707,372 A | 1/1998 | Errico | |
| 5,709,684 A | 1/1998 | Errico | |
| 5,709,685 A | 1/1998 | Dombrowski | |
| 5,716,355 A | 2/1998 | Jackson et al. | |
| 5,716,356 A | 2/1998 | Biedermann | |
| 5,727,899 A | 3/1998 | Dobrovolny | |
| 5,733,285 A | 3/1998 | Errico | |
| 5,733,286 A | 3/1998 | Errico | |
| 5,735,850 A | 4/1998 | Baumgartner | |
| 5,735,851 A | 4/1998 | Errico | |
| 5,735,853 A | 4/1998 | Olerud | |
| 5,741,254 A | 4/1998 | Henry et al. | |
| 5,741,255 A | 4/1998 | Krag | |
| 5,743,911 A | 4/1998 | Cotrel | |
| 5,746,741 A | 5/1998 | Kraus et al. | |
| 5,752,955 A | 5/1998 | Errico | |
| 5,800,548 A | 9/1998 | Martin et al. | |
| 5,810,816 A | 9/1998 | Roussouly | |
| 5,814,046 A | 9/1998 | Hopf | |
| 5,855,284 A | 1/1999 | Dembicks | |
| 5,876,403 A | 3/1999 | Shitoto | |
| 5,899,903 A | 5/1999 | Cotrel | |
| 5,928,231 A | 7/1999 | Klein | |
| 5,938,663 A | 8/1999 | Petreto | |
| 5,947,965 A | 9/1999 | Bryan | |
| 5,947,966 A | 9/1999 | Drewry et al. | |
| 5,947,967 A | 9/1999 | Barker | |
| 5,976,133 A | 11/1999 | Kraus et al. | |
| 5,976,135 A | 11/1999 | Sherman | |
| 5,980,521 A | 11/1999 | Montague | |
| 5,980,523 A | 11/1999 | Jackson | |
| 5,984,922 A | 11/1999 | McKay | |
| 5,984,923 A | 11/1999 | Breard | |
| 5,984,924 A | 11/1999 | Asher | |
| 5,989,250 A | 11/1999 | Wagner et al. | |
| 5,989,251 A | 11/1999 | Nichols | |
| 5,997,539 A | 12/1999 | Errico | |
| 6,027,533 A | 2/2000 | Olerud | |
| 6,030,388 A | 2/2000 | Yoshimi | |
| 6,050,997 A | 4/2000 | Mullane | |
| 6,063,090 A | 5/2000 | Schlapfer | |
| 6,077,262 A | 6/2000 | Schlapfer | |
| 6,080,156 A | 6/2000 | Asher | |
| 6,083,226 A | 7/2000 | Fiz | |
| 6,090,110 A | 7/2000 | Metz-Stavenhagen | |
| 6,096,039 A | 8/2000 | Stoltenberg | |
| 6,110,173 A | 8/2000 | Thomas | |
| 6,113,600 A | 9/2000 | Drummond et al. | |
| 6,113,601 A | 9/2000 | Tatar | |
| 6,132,430 A | 10/2000 | Wagner | |
| 6,136,003 A | 10/2000 | Hoeck | |
| 6,139,548 A | 10/2000 | Errico | |
| 6,171,311 B1 | 1/2001 | Richelsoph | |
| 6,176,861 B1 | 1/2001 | Bernstein | |
| 6,179,838 B1 | 1/2001 | Fiz | |
| 6,179,841 B1 | 1/2001 | Jackson | |
| 6,183,473 B1 | 2/2001 | Ashman | |
| 6,187,005 B1 | 2/2001 | Brace | |
| 6,210,413 B1 | 4/2001 | Justis | |
| 6,214,006 B1 | 4/2001 | Metz Stavenhagen | |
| 6,217,578 B1 | 4/2001 | Crozet | |
| 6,231,575 B1 | 5/2001 | Krag | |

| | | | | | | |
|---|---|---|---|---|---|---|
| 6,234,705 | B1 | 5/2001 | Troxell | 6,887,241 B1 | 5/2005 | McBride et al. |
| 6,238,396 | B1 * | 5/2001 | Lombardo ............... 606/86 A | 6,964,665 B2 | 11/2005 | Thomas |
| 6,254,602 | B1 | 7/2001 | Justis | 7,008,423 B2 | 3/2006 | Assaker |
| 6,254,603 | B1 | 7/2001 | Gertzbein | 7,033,358 B2 | 4/2006 | Taylor et al. |
| 6,258,090 | B1 | 7/2001 | Jackson | 7,081,116 B1 | 7/2006 | Carli |
| 6,261,287 | B1 | 7/2001 | Metz Stavenhagen | 7,122,036 B2 | 10/2006 | Vanacker |
| 6,264,658 | B1 | 7/2001 | Lee | 7,128,743 B2 | 10/2006 | Metz-Stavenhagen |
| 6,267,765 | B1 | 7/2001 | Taylor | 7,137,986 B2 | 11/2006 | Troxell et al. |
| 6,273,888 | B1 | 8/2001 | Justis | 7,166,108 B2 | 1/2007 | Mazda et al. |
| 6,280,442 | B1 | 8/2001 | Barker | 7,270,665 B2 | 9/2007 | Morrison |
| 6,280,443 | B1 | 8/2001 | Gu | 7,314,467 B2 | 1/2008 | Howland |
| 6,280,445 | B1 | 8/2001 | Morrison | 2002/0035366 A1 | 3/2002 | Walder |
| 6,283,967 | B1 | 9/2001 | Troxell | 2002/0143327 A1 | 10/2002 | Shluzas |
| 6,287,308 | B1 | 9/2001 | Betz | 2003/0004512 A1 | 1/2003 | Farris |
| 6,287,309 | B1 | 9/2001 | Baccelli | 2003/0060823 A1 | 3/2003 | Bryan |
| 6,287,311 | B1 | 9/2001 | Sherman | 2003/0114853 A1 | 6/2003 | Burgess et al. |
| 6,290,700 | B1 | 9/2001 | Schmotzer | 2004/0044344 A1 | 3/2004 | Winquist |
| 6,290,703 | B1 | 9/2001 | Ganem | 2004/0092930 A1 | 5/2004 | Petit et al. |
| 6,299,614 | B1 | 10/2001 | Kretschmer | 2004/0116928 A1 | 6/2004 | Young |
| 6,302,882 | B1 | 10/2001 | Lin et al. | 2004/0133202 A1 | 7/2004 | Suzuki et al. |
| 6,302,888 | B1 | 10/2001 | Mellinger | 2004/0133203 A1 | 7/2004 | Young |
| 6,306,137 | B2 | 10/2001 | Troxell | 2004/0260285 A1 | 12/2004 | Steib |
| 6,309,135 | B1 | 10/2001 | Thomson et al. | 2005/0080416 A1 | 4/2005 | Ryan et al. |
| 6,309,390 | B1 | 10/2001 | Le Couedic | 2005/0080419 A1 | 4/2005 | Donath |
| 6,309,391 | B1 | 10/2001 | Crandall | 2005/0090821 A1 * | 4/2005 | Berrevoets et al. ............ 606/61 |
| 6,326,740 | B1 | 12/2001 | Chang | 2005/0107789 A1 | 5/2005 | Sweeney |
| 6,328,740 | B1 | 12/2001 | Richelsoph | 2005/0228377 A1 | 10/2005 | Chao et al. |
| 6,328,741 | B1 | 12/2001 | Richelsoph | 2006/0058789 A1 * | 3/2006 | Kim et al. ................ 606/61 |
| 6,361,535 | B2 | 3/2002 | Jackson | 2006/0064093 A1 | 3/2006 | Thramann et al. |
| 6,368,319 | B1 | 4/2002 | Schaefer | 2006/0084996 A1 | 4/2006 | Metz-Stavenhagen |
| 6,368,321 | B1 | 4/2002 | Jackson | 2006/0206114 A1 | 9/2006 | Ensign et al. |
| 6,371,957 | B1 | 4/2002 | Amrein | 2006/0217712 A1 | 9/2006 | Mueller et al. |
| 6,375,657 | B1 | 4/2002 | Doubler | 2006/0233597 A1 | 10/2006 | Ensign et al. |
| 6,379,354 | B1 | 4/2002 | Rogozinski | 2006/0247622 A1 | 11/2006 | Maughan et al. |
| 6,379,357 | B1 | 4/2002 | Bernstein | 2006/0271045 A1 * | 11/2006 | Hubbard et al. ............ 606/61 |
| 6,402,751 | B1 | 6/2002 | Hoeck et al. | 2006/0271051 A1 | 11/2006 | Berrevoets et al. |
| 6,443,953 | B1 | 9/2002 | Perra | 2007/0049932 A1 * | 3/2007 | Richelsoph et al. ............ 606/61 |
| 6,458,132 | B2 | 10/2002 | Choi | 2007/0213721 A1 * | 9/2007 | Markworth et al. ............ 606/61 |
| 6,471,705 | B1 | 10/2002 | Biedermann | 2007/0213723 A1 * | 9/2007 | Markworth et al. ............ 606/61 |
| 6,524,310 | B1 * | 2/2003 | Lombardo et al. .......... 606/250 | 2007/0276384 A1 * | 11/2007 | Spratt ................. 606/72 |
| 6,537,276 | B2 | 3/2003 | Metz Stavenhagen | 2008/0086134 A1 * | 4/2008 | Butler et al. .............. 606/64 |
| 6,554,832 | B2 | 4/2003 | Shluzas | | | |
| 6,565,568 | B1 | 5/2003 | Rogozinski | FOREIGN PATENT DOCUMENTS | | |
| 6,565,569 | B1 | 5/2003 | Assaker | DE | 2 98 08 593 | 10/1999 |
| 6,569,164 | B1 | 5/2003 | Assaker | DE | 1 99 57 332 | 11/1999 |
| 6,572,618 | B1 | 6/2003 | Morrison | EP | 0 466 092 | 7/1991 |
| 6,574,789 | B1 | 6/2003 | Yamauchi | EP | 0 536 066 | 9/1992 |
| 7,322,979 | B2 | 6/2003 | Crandall | EP | 0 596 788 | 10/1993 |
| 6,602,253 | B2 | 8/2003 | Richelsoph et al. | EP | 0 734 688 | 2/1996 |
| 6,610,063 | B2 | 8/2003 | Kumar | EP | 0 793 947 A1 | 9/1997 |
| 6,616,668 | B2 | 9/2003 | Altarac et al. | EP | 0 836 836 | 4/1998 |
| 6,618,960 | B2 | 9/2003 | Brown | EP | 0 878 170 A2 | 11/1998 |
| 6,620,164 | B2 | 9/2003 | Ueyama | EP | 0 956 829 | 11/1999 |
| 6,626,908 | B2 | 9/2003 | Cooper | EP | 1 093 761 | 4/2001 |
| 6,652,535 | B2 | 11/2003 | Kvarnstrom et al. | EP | 1 103 226 | 5/2001 |
| 6,673,073 | B1 | 1/2004 | Schafer | EP | 0 746 255 B1 | 9/2002 |
| 6,685,705 | B1 | 2/2004 | Taylor | FR | 2 697 742 | 5/1994 |
| 6,699,248 | B2 | 3/2004 | Jackson | FR | 2 781 359 A1 | 8/2000 |
| 6,736,816 | B2 | 5/2004 | Ritland | FR | 2 804 314 A1 | 8/2001 |
| 6,736,817 | B2 | 5/2004 | Troxell et al. | WO | 91/01115 | 2/1991 |
| 6,736,820 | B2 | 5/2004 | Biedermann | WO | 91/06254 | 5/1991 |
| 6,740,086 | B2 | 5/2004 | Richelsoph | WO | 93/11715 | 6/1993 |
| 6,749,361 | B2 | 6/2004 | Hermann et al. | WO | 93/21847 | 11/1993 |
| 6,749,612 | B1 | 6/2004 | Conchy et al. | WO | 94/00062 | 1/1994 |
| 6,749,613 | B1 | 6/2004 | Conchy et al. | WO | 94/00066 | 1/1994 |
| 6,758,545 | B2 | 7/2004 | Ikeda | WO | 94/06361 | 3/1994 |
| 6,770,075 | B2 | 8/2004 | Howland | WO | 94/08530 | 4/1994 |
| 6,773,214 | B2 | 8/2004 | Jakubowski, Jr. et al. | WO | 94/14384 | 7/1994 |
| 6,783,526 | B1 | 8/2004 | Lin et al. | WO | 94/20048 | 9/1994 |
| 6,786,907 | B2 | 9/2004 | Lange | WO | 95/02372 | 1/1995 |
| 6,872,208 | B1 | 3/2005 | McBride et al. | WO | 95/08298 | 3/1995 |
| 6,872,209 | B2 | 3/2005 | Morrison | WO | 95/13753 | 5/1995 |
| 6,875,211 | B2 | 4/2005 | Nichols et al. | | | |

| | | | | | | |
|---|---|---|---|---|---|---|
| WO | 95/13754 | 5/1995 | | WO | 01/01873 | 1/2001 |
| WO | 95/13755 | 5/1995 | | WO | 01/06939 | 2/2001 |
| WO | 95/13756 | 5/1995 | | WO | 01/06940 | 2/2001 |
| WO | 95/25473 | 9/1995 | | WO | 01/08574 | 2/2001 |
| WO | 95/26687 | 10/1995 | | WO | 01/10317 | 2/2001 |
| WO | 95/28889 | 11/1995 | | WO | 01/15612 | 3/2001 |
| WO | 95/31147 | 11/1995 | | WO | 01/19266 | 3/2001 |
| WO | 95/35067 | 12/1995 | | WO | 00/54681 | 4/2001 |
| WO | 96/02200 | 2/1996 | | WO | 01/24718 | 4/2001 |
| WO | 96/27334 | 9/1996 | | WO | 01/39677 | 6/2001 |
| WO | 96/28106 | 9/1996 | | WO | 01/52756 | 7/2001 |
| WO | 96/32070 | 10/1996 | | WO | 01/52757 | 7/2001 |
| WO | 96/36291 | 11/1996 | | WO | 01/52758 | 7/2001 |
| WO | 96/39090 | 12/1996 | | WO | 01/54597 | 8/2001 |
| WO | 96/39972 | 12/1996 | | WO | 01/58369 | 8/2001 |
| WO | 96/41582 | 12/1996 | | WO | 01/67972 | 9/2001 |
| WO | 97/06742 | 2/1997 | | WO | 01/67973 | 9/2001 |
| WO | 97/14368 | 4/1997 | | WO | 01/78613 | 10/2001 |
| WO | 97/23170 | 7/1997 | | WO | 01/91656 | 12/2001 |
| WO | 97/31579 | 9/1997 | | WO | 02/00124 | 1/2002 |
| WO | 97/31580 | 9/1997 | | WO | 02/00125 | 1/2002 |
| WO | 97/38640 | 10/1997 | | WO | 02/00126 | 1/2002 |
| WO | 97/43974 | 11/1997 | | WO | 02/02024 | 1/2002 |
| WO | 98/15233 | 4/1998 | | WO | 02/09603 | 2/2002 |
| WO | 98/17188 | 4/1998 | | WO | 02/15766 | 2/2002 |
| WO | 98/37824 | 9/1998 | | WO | 02/30307 | 4/2002 |
| WO | 98/43551 | 10/1998 | | WO | 02/34149 | 5/2002 |
| WO | 98/55038 | 12/1998 | | WO | 02/34151 | 5/2002 |
| WO | 99/00065 | 1/1999 | | WO | 02/38060 | 5/2002 |
| WO | 99/03415 | 1/1999 | | WO | 02/38061 | 5/2002 |
| WO | 99/09901 | 3/1999 | | WO | 02/38063 | 5/2002 |
| WO | 99/15094 | 4/1999 | | WO | 02/41797 | 5/2002 |
| WO | 99/18874 | 4/1999 | | WO | 02/45606 | 6/2002 |
| WO | 99/29248 | 6/1999 | | WO | 02/45607 | 6/2002 |
| WO | 99/49802 | 10/1999 | | WO | 02/078517 | 10/2002 |
| WO | 99/55246 | 11/1999 | | WO | 02/090604 | 11/2002 |
| WO | 99/55247 | 11/1999 | | WO | 02/091931 | 11/2002 |
| WO | 99/56652 | 11/1999 | | WO | 03/037198 | 5/2003 |
| WO | 00/06038 | 2/2000 | | WO | 03/068087 | 8/2003 |
| WO | 00/14568 | 3/2000 | | WO | 03/099148 | 12/2003 |
| WO | 00/15125 | 3/2000 | | WO | 2004/010881 | 2/2004 |
| WO | 00/15126 | 3/2000 | | WO | 2004/021902 | 3/2004 |
| WO | 00/16710 | 3/2000 | | WO | 2004/039268 | 5/2004 |
| WO | 00/21447 | 4/2000 | | WO | 2004/039269 | 5/2004 |
| WO | 00/21477 | 4/2000 | | WO | 2004/096065 | 11/2004 |
| WO | 00/25689 | 5/2000 | | WO | 2004/110289 | 12/2004 |
| WO | 00/42930 | 7/2000 | | WO | 2004/112626 | 12/2004 |
| WO | 00/48523 | 8/2000 | | | | |
| WO | 00/57801 | 10/2000 | | | | |
| WO | 00/59387 | 10/2000 | | | | |
| WO | 00/62691 | 10/2000 | | | | |
| WO | 00/62692 | 10/2000 | | | | |
| WO | 00/72769 | 12/2000 | | | | |
| WO | 00/72770 | 12/2000 | | | | |
| WO | 00/76413 | 12/2000 | | | | |
| WO | 01/01872 | 1/2001 | | | | |

OTHER PUBLICATIONS

Non-Final Office Action Dated Nov. 26, 2008 for U.S. Appl. No. 11/221,512, filed Sep. 8, 2005.
Final Office Action Dated May 29, 2009 for U.S. Appl. No. 11/221,512, filed Sep. 8, 2005.

* cited by examiner

*FIG.5*

ROD TO ROD CONNECTOR

RELATED APPLICATION

This application claims the benefit of U.S. Provisional Application No. 60/870,856, filed Dec. 20, 2006, which is incorporated by reference herein.

BACKGROUND

1. Field of the Invention

The invention generally relates to orthopedic devices. More specifically, the invention pertains to surgical implants used with spinal rods for the purpose of spinal fixation and correction of spinal curvature.

2. Description of Related Art

Spinal rods are often used for spinal fixation, including for correction of scoliotic curves. Fixation often involves implantation of such rods by attaching them to the spine with anchors in the form of hooks and/or pedicle screws. Often, a pair of rods are placed on opposite sides of the spine.

Various systems have been developed for rigidly connecting two spinal rods together to prevent rod migration and to increase stiffness of the paired rod assembly. In many cases involving multi-level fusion of the spine, these features are highly beneficial while stabilizing the spine construct until solid bone fusion is accomplished. In the post-operative period before fusion occurs, a significant amount of motion can occur between the rods, wires and hooks, which can, for example, allow a scoliotic correlation to decrease or the pelvis to de-rotate toward its previous, deformed position. By providing a rigid transverse connection between two spinal rods, the loss of correction can be reduced and a stiffer construct can be created, which may enhance the promotion of solid fusion.

It is sometimes the case that the two side-by-side spinal rods that are to be interconnected by a rod to rod connector are not perfectly parallel to each other. This is a problem for many rod to rod connectors of the prior art which do not permit for any angle between the two spinal rods.

SUMMARY OF THE INVENTION

An apparatus for coupling a spinal rod to a cross bar comprising a main body having a channel with a wall for receiving a spinal rod therein, an opening for receiving a fastener with at least one tang adjacent to the opening, a clamping body disposed in the main body, the clamping body being moveable between a first position in which it does not clamp the spinal rod in the channel and a second position in which it does clamp the spinal rod in the channel, a cross bar having an opening aligned substantially with the opening of the main body and having the tang disposed therein, and a fastener for rigidly coupling the cross bar to the main body, the fastener being positioned within the openings of the cross bar and the main body, wherein the fastener is operable to force the tang into the cross bar to clamp the cross bar to the main body and simultaneously to move the clamping body between the first position and the second position.

DETAILED DESCRIPTION OF THE INVENTION

Figure 1:
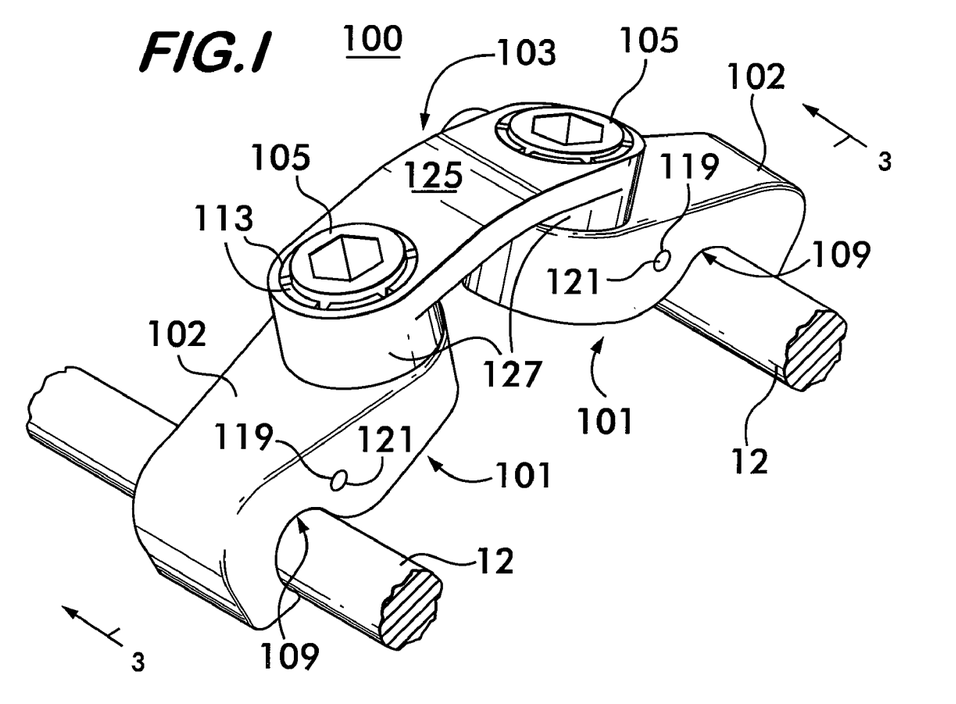
FIG. 1 is a perspective view of a rod to rod connector in accordance with one embodiment of the present invention in an assembled condition.
Figure 2:
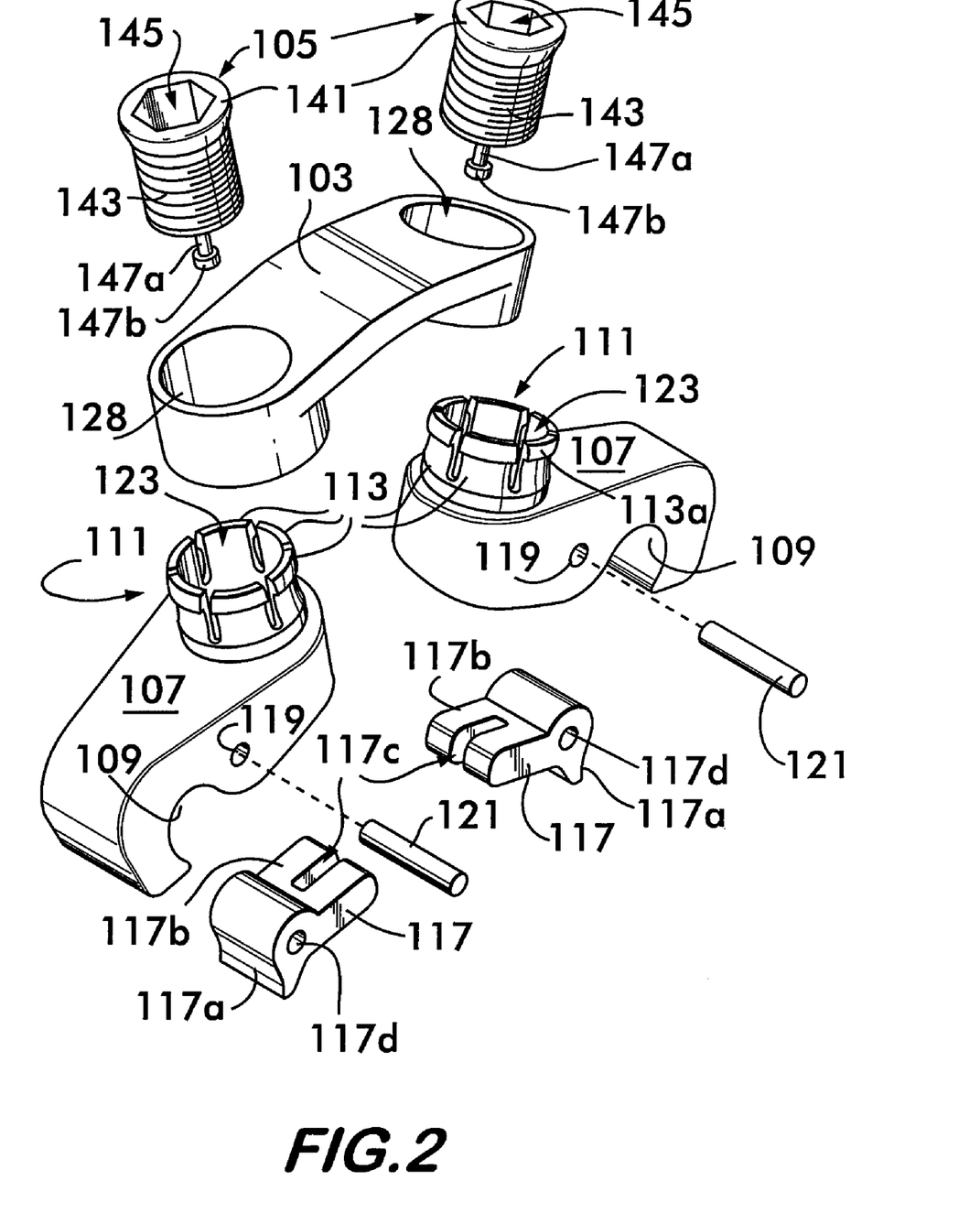
FIG. 2 is an exploded perspective view of the rod to rod connector of FIG. 1.
Figure 3:
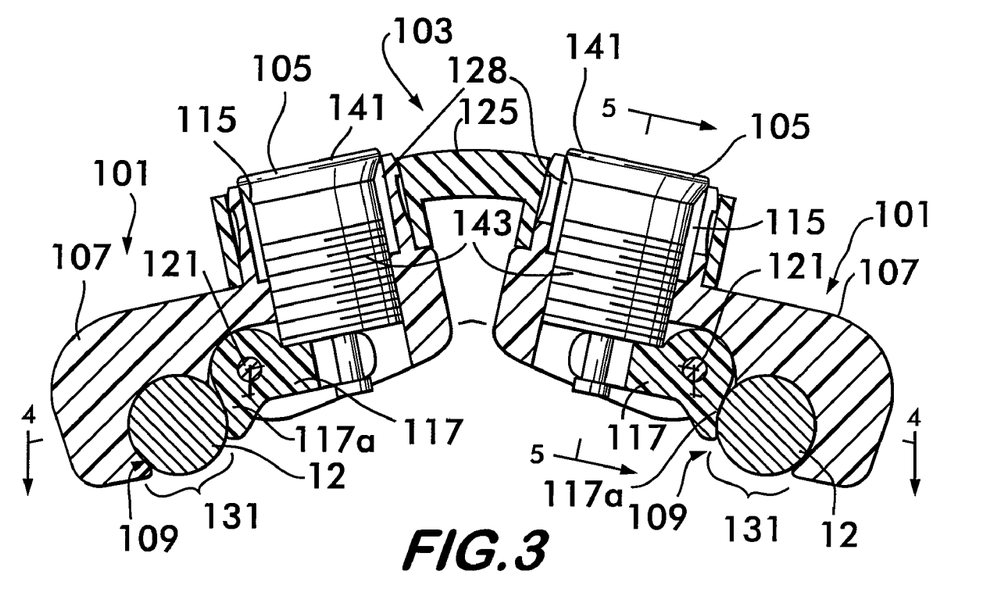
FIG. 3 is a cross sectional view of the rod to rod connector of FIG. 1 taken along line 3-3 in FIG. 1.

FIGS. 1-5 illustrate a rod to rod connector 100 in accordance with a first embodiment of the invention. FIG. 1 is a perspective view of the rod to rod connector 100 for rigidly connecting two spinal rods 12, 12, to each other in an assembled state. The two rods may, for instance, be positioned substantially parallel with each other on opposite sides of the spine. FIG. 2 is an exploded view of the elements of the same rod to rod connector. The cross connector 100 comprises two rod clamps 101, a cross bar 103, and two fasteners in the form of set screws 105 in this particular embodiment.

The cross bar 103 comprises a transverse beam portion 125 connecting two connecting portions 127, 127 at opposite ends of the cross bar. The connecting portions 127, 127 include holes 128, 128. The cross bar may be curved or angled, such as in the shape of a V as shown in the Figures to better accommodate the space requirements when crossing the centerline of the spine.

Each rod clamp 101 comprises a main body portion 107, a rod receiving channel 109, and a tang (or tulip) portion 111. The rod clamp 101 includes a hole 123. Preferably, the wall of the rod receiving channel has the same radius as the spinal rod with which the apparatus is to be used. The lateral opening 131 into the rod receiving channel 109 is larger than the diameter of the spinal rod 12 so that a spinal rod may be introduced into the channel through opening 131. A pivot body such as cam clamp 117 is disposed within the main body portion and is supported on a pivot pin 121 disposed within a transverse hole 119 in the main body portion. The cam clamp includes a curved surface 117a that faces into the rod receiving channel 109 and generally matches the arc of the rod receiving channel 109. It also includes a lever portion 117b extending in the opposite direction from the pivot pin from the curved surface 117a and a transverse hole 117d for accepting the pivot pin 121. The lever portion 117b includes a slot 117c. When the cam clamp 117 is rotated about the pivot pin 121 to cause the curved surface 117a to enter the rod receiving channel and engage the rod in the channel, it effectively prevents the rod from escaping from the rod receiving channel.

The tulip portion comprises a plurality of tangs 113 extending upwardly from the main body portion 107 defining an extension of the hole 123. The tangs include outwardly extending flanges or barbs 113a at their tops. The holes 123 preferably extend completely through the main body portion 107. The bottom portion of the hole 123 that is within the main body portion 107 of the rod clamp 101 is threaded to accept mating threads of the corresponding set screw 105 to couple the cross bar 105 to the rod clamp 101. The cylinder that is defined by the outer surfaces of the tangs 113 on the rod clamp 101 when they are in an unstressed condition is smaller than the cylinder defined by through holes 128 of the connecting portions 127 of the cross bar 103.

The set screws 105 include a threaded shank portion 143 and a head portion 141 having a diameter larger than the diameter of the threaded shaft portion. More specifically, the head portion 141 has a diameter wider than the cylindrical space defined between the tangs of the rod clamp and the shank 143 has a diameter equal to or smaller than the cylindrical space defined between the tangs 113 on the rod clamp 101. The threaded shank is designed to mate with internal threads in the bottom portion of the hole 128 in the main body portion 107 of the rod clamp 101. The head portion 141 of the set screw 105 includes a feature 145 for accepting a torque-applying tool for rotating the screw. In the exemplary embodiment it is shown as a hexagonally shaped blind aperture for accepting a hex wrench or hex screw driver.

A locking mechanism 147 comprising a thin post 147a extends longitudinally from the bottom of the threaded shank 143 of the set screw 105 and has an enlarged button or head 147b at its end. In one embodiment, the head is pre-formed such as by machining or casting. In another embodiment, the post 147a is first formed without the head and the end of the post is peened to form the head 147b either before assembly of the cross connector or, as described below, after assembly.

Figure 4:
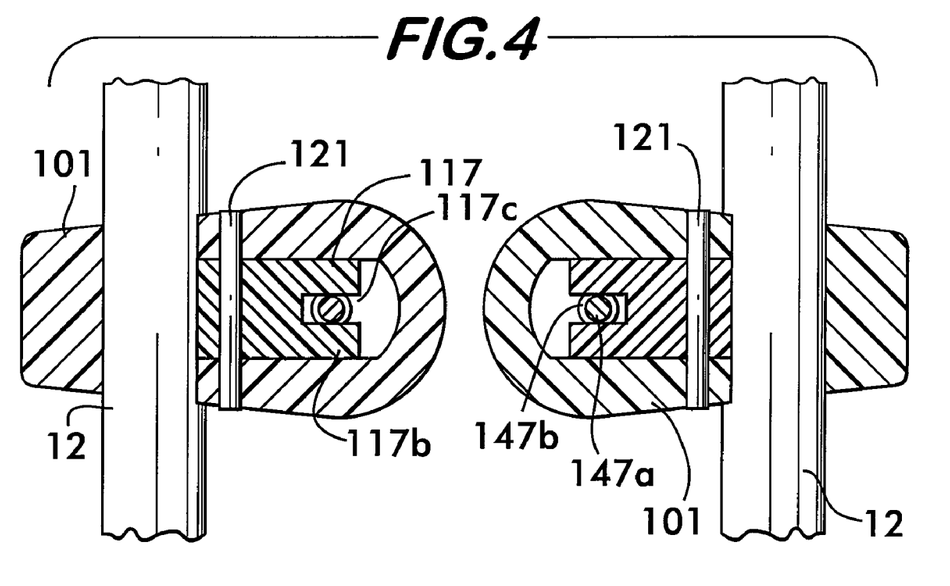
FIG. 4 is a partially cross sectional plan view of the rod to rod connector of FIG. 1 taken along line 4-4 in FIG. 3 illustrating the construction of the set screws, rotations pins, and cam clamps.
Figure 5:
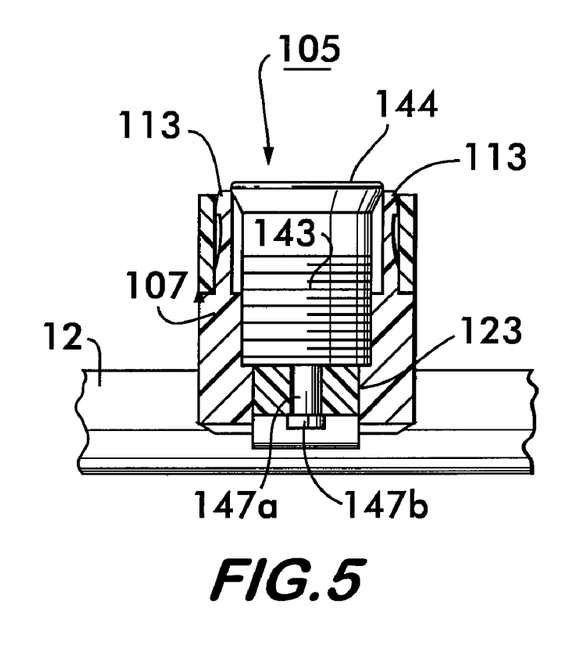
FIG. 5 is a partially cross sectional side view of the rod to rod connector of FIG. 1 taken along line 5-5 in FIG. 3 illustrating the set screw in the tulip portion of the clamp.

In the assembled state, the thin post 147a extends through the slot 117c in the cam clamp 117 with the enlarged head 147b extending from the bottom of the slot. The enlarged head 147b has a diameter (or other profile) larger than the width of the slot 117c so that the head cannot pass through the slot. Also, the threaded shank 143 of the set screw 105 also has a diameter larger than the width of the slot 117c so that it also cannot pass through the slot in the longitudinal direction of the screw, but is trapped in the slot. However, the screw 105 can rotate about its longitudinal axis freely relative to the cam clamp 117. This is best seen in FIGS. 4 and 5, which are cross sectional views taken along lines 4-4 and 5-5, respectively in FIG. 3. Therefore, when the device is assembled, the set screw 105 will be positively connected with the cam clamp 117 (i.e., the post 147a is trapped in the slot 117c such that longitudinal movement of the screw 105 in either longitudinal direction will translate into pivoting of the cam clamp 117 in one or the other direction). Therefore, the screw 105, not only can force the cam clamp 117 to clamp the rod 12 when the screw is advanced into the hole 128, but can also hold the cam clamp 117 out of the rod receiving channel 109 when the screw is withdrawn to permit the rod 12 to freely slip into the rod receiving channel. Also, the screw 105 cannot accidentally fall out of or otherwise be removed from the cross connector 100 even if its threads become disengaged from the threads in the hole. In fact, the length of the thread run on the screw 105 can be selected so that the threads could not become disengaged after the apparatus is assembled and the post 147a is trapped in the slot 117c of the cam clamp.

Preferably, the length of the thin post 147a between the bottom of the threaded shank 143 of the screw and the head 147b is slightly greater than the depth of the slot 117c so that there is some "play" or flexibility in the connection between the cam clamp 117 and the set screw 105. Particularly, the cam clamp 117 must rotate about the pivot axis of the pivot pin 121 in response to linear movement of the set screw 105. Therefore, the connection cannot be so tight as to interfere with the free rotation of the cam clamp and must be at least somewhat flexible.

In alternative embodiments, the pivot body 117 can be replaced with a translatable body disposed in the main body 101. The translatable body may be captured within a channel in the main body so that it cannot fall out inadvertently during surgery. For instance, a translatable body may be slidable in the channel under the urging of the set screw 105 (or other fastener) between a locking position, in which it partially closes the opening 131 and engages the rod so as to lock it rigidly in the channel, and an open position, in which it is substantially out of the opening 131, permitting the rod to freely pass through the opening 131. The movement of the translatable body may be substantially linear or curved. Like the pivot body 117, the translatable body may be attached to the fastener, such as through a flexible connection, so that movement of the fastener in either direction causes movement of the translatable body. Alternately, the translatable body (or pivot body) may butt up against the translatable body (or pivot body) such that it can only push the body, rather than push and pull it.

To assemble the cross connector in a loose, pre-operative state, first the cross bar 103 is dropped onto the clamping bodies 101 so that the through holes 128 in the connecting portions 127 of the cross bar surround the tangs 113 of the clamping bodies and align with the holes 123 in the clamping bodies. At this point, the clamping bodies 101 can rotate relative to the cross bar 103 around the axis defined by the aligned through holes 128 and holes 127 because, as previously mentioned, the through holes 128 in the cross bar 103 have a larger diameter than the cylinder defined by the outer surfaces of the tangs 113 when the tangs are in an unstressed condition.

In a preferred embodiment of the invention, the connecting portions have a height that approximately matches the height of the tangs 113. The connecting portions 127 may have a height that is greater than the height of the transverse beam portion 125, which can be much thinner while still providing more than adequate strength.

Next, the set screws 105 are inserted into the through holes 128 in the connecting portions 127 of the cross bar 103 and screwed partially into the holes 123 in the rod clamp 101 so that the post 147a extending from the bottom of the set screw 105 is disposed in the lower portion of the rod clamp 101, but the head 141 is above the tangs. The cam clamp 117 can then be inserted into position in the main body 107 until the transverse hole 117d in the cam clamp 117 aligns with the transverse hole 119 in the main body 107 and, simultaneously, the thin post 147a of the locking mechanism 147 of the set screw 105 fits within the slot 117c in the cam clamp. If the head 147b is not pre-formed, the cam clamp 117 can be installed before or after the set screw 105 is inserted. If after, the cam clamp 117 slid essentially straight upwardly into the main body portion so that the slot 117c slides over the thin post 147a until the end of the post extends through the bottom of the slot 117c. Then the distal end of the post 147a extending from the bottom of the slot can be peened to enlarge it into the head 147b. If the head is pre-formed then, depending on the particular design of the opening within which the cam clamp fits, the cam clamp may need to be inserted via a more complicated maneuver (since the head itself cannot fit through the slot).

The pivot pin can then be installed through the aligned holes 119 and 117d. The pivot pin, for example, may be affixed in the aligned holes by an interference fit with either the hole 119 in the main body or the hole 117d of the cam clamp (but not both). Hence, the pivot pin will be fixed in the main body and incapable of accidentally falling out or otherwise being removed unintentionally, but the cam clamp can rotate about the pivot pin 121 relative to the main body portion 101.

At this point, the cross connector is fully assembled in the loose, pre-operative state. In this condition, the clamping bodies 101 can rotate relative to the cross bar 103 about the longitudinal axes of the set screws 105 so as to accommodate different orientations between the two spinal rods 12 in the saggital plane. Also, the cam clamp 117 is pivoted to an open position (i.e., with the cam clamp not extending into the rod receiving channel 109) so that the cross connector 100 can be dropped onto the spinal rods 12 and the spinal rods will slide easily into the rod receiving channels 109.

After the surgeon has placed the cross connector 100 onto the two rods 12 as just described, the entire assembly can be tightened and locked by tightening the two set screws 105 to lock the spinal rods 12 rigidly in the rod receiving channels 109 and simultaneously lock the orientations of the clamping bodies 101 relative to the cross bar 103. Particularly, rotating each set screw 105 so as to advance it into the hole 123 by means of the mutual engagement of the internal threads of the holes 123 in the main body portion 107 with the external threads of the shank 143 of the set screw will cause the head 141 of the set screw 105 to engage the tangs 113 and force them to resiliently bend radially outwardly, whereupon the outer surfaces of the flanges 113a will squeeze against the inner wall of the through holes 128 of the cross bar 101. In one embodiment as shown in the Figures, the bottom of the head forms a wedge tapered down to the shank diameter so that, as the head moves downwardly after engaging the tangs, the tangs will be increasingly bent outwardly. In one embodiment, the flanges or barbs 113a on the tangs have relatively sharp edges to bite into the internal walls of the through holes 128 to provide an even stronger resistance to rotation.

Simultaneously, as the set screw 105 advances into the hole 123 in the main body 107, the locking mechanism 147 forces the cam clamp 117 to rotate forwardly into the rod receiving channel 109 so that the curved surface 117a engages the rod 12 in the rod receiving channel rigidly locking the rod therein.

In alternate embodiments of the invention, the set screw 105 may connect to the main body portion in other ways than a threaded engagement. For instance, it may connect by means of a bayonet connection wherein the shank of the set screw has a pin other protrusion extending radially from it that mates with a slot, groove or other recess on the wall of the hole 123. Merely as one example, a slot on the wall of the hole 123 would have one open end at the top of the hole 123 and could be contoured to have a portion extending in the longitudinal direction of the screw starting at the opening followed by a portion that is substantially, but not perfectly perpendicular thereto that terminates in a locking recess at its closed end essentially just large enough to fit the pin. Therefore, when the screw is advanced into the hole so the pin reaches the end of the longitudinal portion of the slot, rotation of the screw would cause the head to slide in the substantially perpendicular portion of the slot causing the screw to longitudinally advance slightly further into the hole. When the head reaches the recess, it will be tightly locked in its final position. Other connection mechanisms also are possible.

Preferably, both of the main clamping bodies 101 are the same. However, it is possible to use rod connecting assemblies of two different designs at the opposite ends of the cross bar 103.

All of the components preferably are made of a biocompatible, resilient material such as titanium, stainless steel, or any number of biocompatible polymers.

Figures 6, 7:
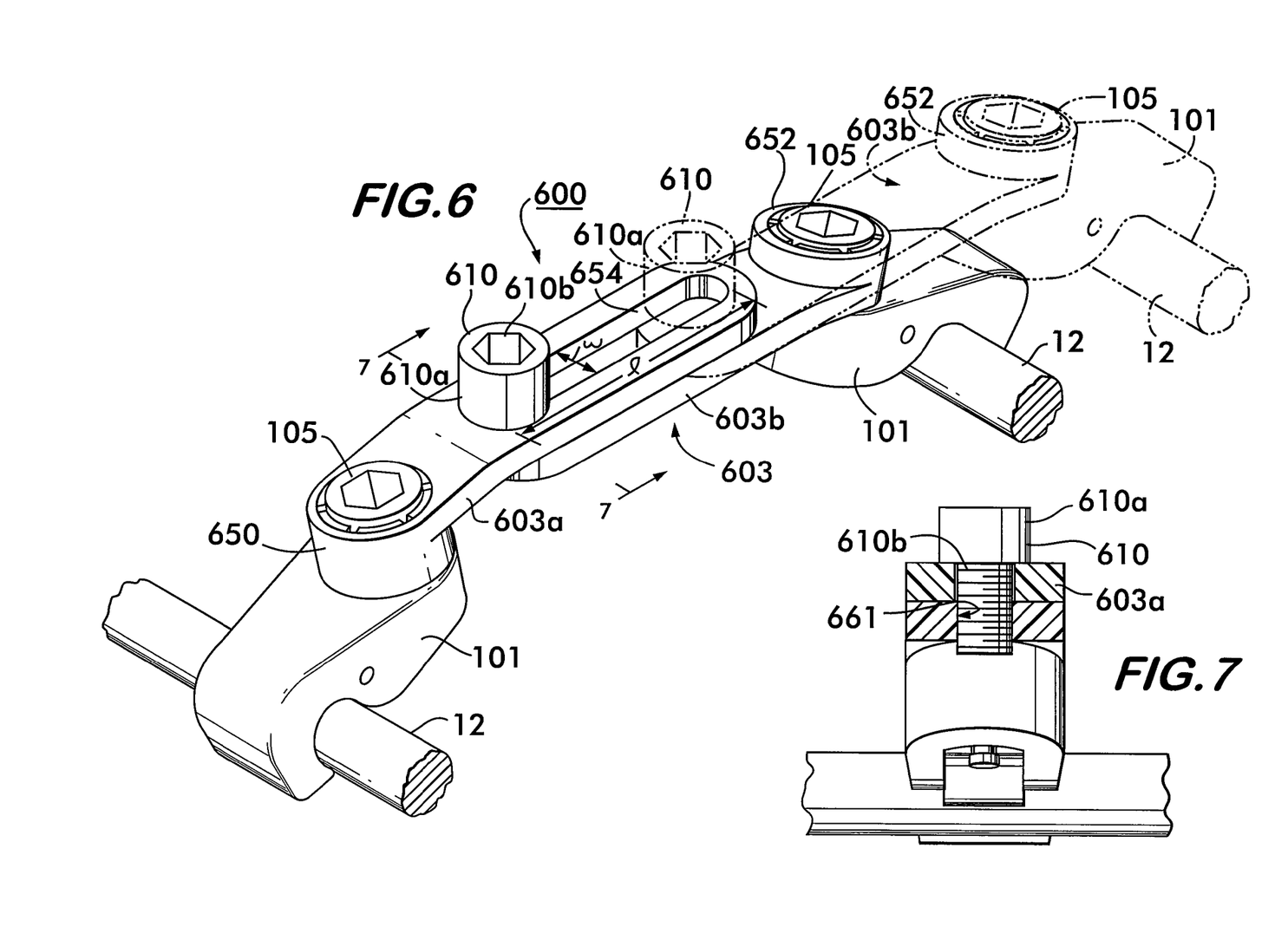
FIG. 6 is a perspective view of rod to rod connector in accordance with another embodiment of the present invention in an assembled condition.
FIG. 7 is a cross sectional view of the rod to rod connector of FIG. 6 taken along line 7-7 in FIG. 6.

The afore-described embodiment of the invention shown in FIGS. 1-5 has a substantially fixed span between the rods. FIGS. 6 and 7 illustrate an alternative embodiment of a cross connector 600 that is variable in length. FIG. 6 is a perspective view of a cross connector in accordance with this embodiment and FIG. 7 is a cross sectional view taken along line 7-7 in FIG. 6. FIG. 6 shows the cross connector 600 set to its minimum length in solid line and also shows the cross connector set to its maximum length in phantom. It also can be set to any length therebetween, as will become clear from the following discussion.

The clamping bodies 101 and set screws 105 (and all of their sub-components) are essentially identical to those described above in connection with the first embodiment.

The cross bar 603 essentially comprises three components, a first cross beam 603a, a second cross beam 603b and a locking screw 610. The locking screw comprises a head 610a and a threaded shank 610b. The head includes a feature 610b for accepting a torque applying tool such as a screw driver, hex driver, wrench, etc for rotating the screw. In a preferred embodiment, the feature is the same as the corresponding feature in the heads 141 of the set screws 105 so that the locking screw 610 can be tightened by the same tool as the set screws.

Each cross beam comprises a connecting portion 650, 652 similar to the connecting portions 127 described in connection with the first embodiment. The cross beam 603a includes an elongate slot 654 having a width slightly greater than the diameter of the threaded shank of the locking screw 610, but smaller than the diameter of the head 610a of the locking screw so that the shank 610b can pass freely through, but the head cannot. The slot 610 has a length greater than its width. The length of the slot 610 essentially defines the variable length range of the cross connector 600.

The cross beam 603b comprises an internally threaded hole 661 near its medial end designed to matingly engage with the external threads of the locking screw 610.

To assemble the cross connector of this embodiment in a loose, pre-operative state, in addition to the procedures discussed above in connection with the first embodiment, the locking screw 610 is inserted through the elongate slot 654 on cross beam 603a and loosely threaded into the threaded aperture 661 in cross beam 603b. The two cross beams 603a, 603b, therefore, are coupled together and inseparable unless the locking screw 610 is removed. However, the two cross beams can slide relative to each other the length of the slot 654. In order to lock the length, the surgeon tightens the locking screw.

Having thus described a few particular embodiments of the invention, various alterations, modifications, and improvements will readily occur to those skilled in the art. Such alterations, modifications and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. An apparatus for coupling a spinal rod to a cross bar comprising:
    a main body having a channel with a wall for receiving a spinal rod therein, an opening for receiving a fastener, and at least one tang adjacent to the opening;
    a clamping body disposed within the main body, the clamping body being moveable between a first position out of the channel in which it does not clamp the spinal rod in the channel and a second position in the channel in which it does clamp the spinal rod in the channel;
    a monolithic cross bar having an opening aligned substantially with the opening of the main body and having the tang disposed therein; and a fastener for rigidly coupling the cross bar to the main body, the fastener being positioned within the openings of the cross bar and the main body, wherein the fastener is operable to force the tang into the cross bar to clamp the cross bar to the main body and simultaneously to move the clamping body between the first position and the second position.

2. The rod to rod connector of claim 1 wherein a portion of the fastener is trapped in a portion of the clamping body.

3. The rod to rod connector of claim 1 wherein the cross bar and the main body are rotatable relative to each other about the fastener prior to operation of the fastener to clamp the cross bar to the main body.

4. The rod to rod connector of claim 1 wherein the fastener comprises a wedge portion and wherein the fastener has a first engagement feature and the opening in the main body has a second engagement feature for mating with the first engagement feature wherein advancement of the fastener into the opening of the main body causes the wedge portion to engage the tang and force the tang into engagement with the cross bar.

5. The rod to rod connector of claim 1, wherein the cross bar comprises a first end with a first connecting portion, a second end with a second connecting portion, and a transverse beam extending between the first connecting portion and the second connecting portion, the first and second connecting portions each forming a cylinder with a longitudinal axis, the transverse beam extending directly between the longitudinal axes of the cylinders.

6. The rod to rod connector of claim 5, wherein the cross bar is bent and the longitudinal axes of the cylinders converge toward one another as they extend away from the cross bar.

7. A rod to rod connector comprising:
a main body having a channel with a wall for receiving a spinal rod therein, an opening for receiving a fastener, and at least one tang adjacent to the opening;
a pivot body pivotally connected to the main body, the pivot body being pivotable so as to clamp the spinal rod between the pivot body and the wall of the channel;
a monolithic cross bar having first and second ends and having an opening adjacent the first end thereof, the opening being aligned substantially with the opening of the main body and having the tang disposed therein;
a fastener for rigidly coupling the cross bar to the main body, the fastener being positioned within the openings of the cross bar and the main body, wherein the fastener is operable to force the tang into the cross bar to clamp the cross bar to the main body and simultaneously pivots the pivot body to clamp the spinal rod; and
an assembly adjacent the second end of the cross bar having a rod receiving channel.

8. The rod to rod connector of claim 7 wherein the pivot body comprises a pivot axis, and further comprising a lever portion and a clamping portion disposed on different sides of the pivot axis, and wherein the fastener engages the lever portion to pivot the pivot body about the pivot axis.

9. The rod to rod connector of claim 8 wherein the fastener comprises a screw.

10. The rod to rod connector of claim 9 wherein the fastener is flexibly coupled to the pivot body.

11. The rod to rod connector of claim 10 wherein the pivot body comprises a slot and the fastener includes a portion trapped in the slot.

12. The rod to rod connector of claim 7 wherein the cross bar and the main body are rotatable relative to each other about the fastener prior to operation of the fastener to clamp the cross bar to the main body.

13. The rod to rod connector of claim 7 wherein the fastener comprises a wedge portion and wherein the fastener has a first engagement feature and the opening in the main body has a second engagement feature for mating with the first engagement feature wherein rotation of the fastener in the opening of the main body advances the fastener into the opening causing the wedge to engage the tang and force the tang into engagement with the cross bar.

14. The rod to rod connector of claim 7 wherein the assembly comprises:
a second main body having a channel with a wall for receiving a second spinal rod therein, an opening for receiving a second fastener, and at least one tang adjacent to the opening; a second pivot body pivotally connected to the main body, the pivot body being pivotable so as to clamp the spinal rod between the pivot body and the wall of the channel; and
wherein the cross bar further comprises a second opening therein adjacent the second end thereof, the second opening being aligned substantially with the opening of the second main body and having the tang disposed therein; and
further comprising a second fastener for rigidly coupling the cross bar to the second main body, the second fastener being positioned within the second opening of the cross bar and the opening of the second main body, wherein the second fastener is operable to force the tang into the cross bar to clamp the cross bar to the second main body and simultaneously pivots the second pivot body to clamp the second spinal rod.

15. The rod to rod connector of claim 14 wherein the fastener comprises a threaded shank having a first diameter and a head having a second diameter greater than the first diameter and wherein the opening in the main body is threaded and wherein rotation of the fastener in the opening of the main body advanced the fastener into the opening causing the head to engage the tang and force it into engagement with the cross bar.

16. A rod to rod connector comprising:
a first body having a first rod receiving channel for receiving a first spinal rod therein, a first clamp including a rod engaging surface, the first clamp pivotably coupled to the first body such that the rod engaging surface is pivotable into the rod receiving channel, the first body further comprising a hole transverse the rod receiving channel and tangs extending from the hole;
a second body having a second rod receiving channel for receiving a second spinal rod therein, a second clamp including a rod engaging surface, the second clamp pivotably coupled to the second body such that the rod engaging surface is pivotable into the rod receiving channel, the second body further comprising a hole transverse the rod receiving channel and tangs extending from the hole;
a monolithic cross bar having a first end with a first hole adjacent the first end, the hole being aligned substantially with the hole of the first body and having the tangs of the first body disposed therein and further having a second end with a second hole adjacent the second end, the second hole being aligned substantially with the hole of the second body and having the tangs of the second body disposed therein;
a first screw positioned within the first hole of the cross bar and the hole of the first body, wherein advancement of the first screw into the hole of the first body forces the tangs of the first body into the cross bar to clamp the cross bar to the first body and simultaneously pivots the first clamp to engage the rod engaging surface with the first spinal rod;

and a second screw positioned within the second hole of the cross bar and the hole of the second body, wherein advancement of the second screw into the hole of the second body forces the tangs of the second body into the cross bar to clamp the cross bar to the second body and simultaneously pivots the second clamp to engage the rod engaging surface with the second spinal rod.

17. The rod to rod connector of claim 16 wherein the cross bar is angled.

18. The rod to rod connector of claim 17 wherein the screw includes a portion trapped in the clamp.

19. The rod to rod connector of claim 16 wherein the first and second clamps each further comprises a pivot axis, a lever portion, and a clamping portion bearing the rod engaging surface, and wherein the first and second screws engage the lever portions of the first and second clamps, respectively, to pivot the clamps about their pivot axes.

20. The rod to rod connector of claim 19 wherein the lever portion of each clamp includes a slot and each of the first and second screws each have respective longitudinal axes and include a portion trapped in but freely rotatable within the slots of the first and second clamps, respectively, whereby movement of the first and second screws along their longitudinal axes causes the first and second clamps, respectively, to pivot about their pivot axes.

21. The rod to rod connector of claim 16 wherein the tangs of each body define a cylindrical space surrounded by the tangs and each of the first and second screws comprises a threaded shank having a first diameter smaller than the cylindrical space defined by the tangs and a head having a second diameter greater than the cylindrical space defined by the tangs, wherein advancing the first and second screws into the holes of the first and second bodies, respectively, causes the head to engage the tangs of the first and second bodies, respectively, and force them to bend radially outwardly into engagement with walls of the first and second holes of the cross bar, respectively.

* * * * *